(12) United States Patent
Johnson

(10) Patent No.: US 10,191,024 B2
(45) Date of Patent: Jan. 29, 2019

(54) ENERGY MANAGEMENT FOR SENSORS

(71) Applicant: Trane International Inc., Davidson, NC (US)

(72) Inventor: Tedd P. Johnson, La Crosse, WI (US)

(73) Assignee: Trane International Inc., Davidson, NC (US)

( * ) Notice: Subject to any disclaimer, the term of this patent is extended or adjusted under 35 U.S.C. 154(b) by 155 days.

(21) Appl. No.: 15/209,200

(22) Filed: Jul. 13, 2016

(65) Prior Publication Data

US 2017/0016869 A1 Jan. 19, 2017

Related U.S. Application Data

(60) Provisional application No. 62/191,645, filed on Jul. 13, 2015.

(51) Int. Cl.
   *G01N 33/00* (2006.01)

(52) U.S. Cl.
   CPC ....... *G01N 33/0073* (2013.01); *G01N 33/004* (2013.01)

(58) Field of Classification Search
   CPC .......... G01N 33/004; G01N 33/0073
   See application file for complete search history.

(56) References Cited

U.S. PATENT DOCUMENTS

| | | | |
|---|---|---|---|
| 4,969,508 A | 11/1990 | Tate et al. | |
| 5,657,317 A | 8/1997 | Mahany et al. | |
| 6,553,336 B1 | 4/2003 | Johnson et al. | |
| 7,437,596 B2 | 10/2008 | McFarland | |
| 7,848,765 B2 | 12/2010 | Phillips et al. | |
| 8,078,324 B2 | 12/2011 | Oakes | |
| 8,199,005 B2 | 6/2012 | Thomas et al. | |
| 8,224,282 B2 | 7/2012 | Songkakul et al. | |
| 8,249,731 B2 | 8/2012 | Tran et al. | |
| 8,332,819 B2 | 12/2012 | McFarland et al. | |
| 8,532,827 B2 | 9/2013 | Stefanski et al. | |
| 8,550,370 B2 | 10/2013 | Barrett et al. | |
| 8,677,342 B1 | 3/2014 | Kidder et al. | |
| 8,981,950 B1 | 3/2015 | Kates | |
| 9,013,324 B2 | 4/2015 | Johnson et al. | |
| 9,077,183 B2 | 7/2015 | Thomas et al. | |
| 2012/0031984 A1 | 2/2012 | Feldmeier et al. | |
| 2012/0179300 A1 | 7/2012 | Warren et al. | |
| 2013/0103204 A1 | 4/2013 | Stefanski et al. | |
| 2013/0201316 A1 | 8/2013 | Binder et al. | |
| 2014/0005839 A1 | 1/2014 | Stefanski et al. | |
| 2014/0203935 A1 | 7/2014 | Kates | |
| 2014/0320295 A1 | 10/2014 | Kates | |
| 2014/0333445 A1 | 11/2014 | Kates | |
| 2015/0045959 A1 | 2/2015 | McPherson | |
| 2015/0077737 A1 | 3/2015 | Belinsky et al. | |
| 2015/0096876 A1 | 4/2015 | Mittleman et al. | |

(Continued)

*Primary Examiner* — David M. Gray
*Assistant Examiner* — Andrew V Do
(74) *Attorney, Agent, or Firm* — The Salerno Law Firm, P.C.

(57) ABSTRACT

The present disclosure is directed to a method for reducing power consumption of a sensor. The method includes determining if a predetermined condition has been met to change at least one of a sensing rate or a sensor resolution, and changing at least one of the sensing rate or sensor resolution if it is determined that the predetermined condition has been met.

22 Claims, 2 Drawing Sheets

(56) References Cited

U.S. PATENT DOCUMENTS

| | | |
|---|---|---|
| 2015/0108901 A1 | 4/2015 | Greene et al. |
| 2015/0170503 A1* | 6/2015 | Wedig .................... G08B 7/066 340/691.5 |
| 2016/0116512 A1* | 4/2016 | Ji ........................ F24F 11/0034 702/61 |

* cited by examiner

ENERGY MANAGEMENT FOR SENSORS

CROSS-REFERENCE TO RELATED APPLICATION

This application claims the benefit of and priority to U.S. Provisional Application Ser. No. 62/191,645 entitled "ENERGY MANAGEMENT FOR SENSORS" and filed Jul. 13, 2015, the entirety of which is hereby incorporated by reference herein for all purposes.

BACKGROUND

1. Technical Field

The present disclosure is directed to systems, apparatus, and methods for improving wireless HVAC components, and in particular, HVAC sensors and HVAC controllers having reduced power consumption, lower manufacturing costs, and increased reliability.

2. Background of Related Art

Heating, ventilation, and air conditioning systems (HVAC systems) typically utilize one or more sensors, thermostats, and/or HVAC controllers to monitor environmental conditions in a building and to operate HVAC equipment installed at the building. Traditional systems utilize components which are interconnected using traditional hard-wiring techniques using electrical conductors routed within the physical structure. Hard-wired systems are generally reliable, but the costs of cabling and installation are high. This is particularly true when installing devices in existing structures where cabling must be snaked through walls and ceilings.

More recently, the use of wireless HVAC devices has become popular since these devices are cheap and easy to install. Existing wireless devices may have drawbacks in that the batteries used in these devices have a limited lifespan and require periodic maintenance and replacement to ensure the HVAC system continues to function reliably. A wireless HVAC device which offers reduced power consumption, lower manufacturing costs, and increased reliability would be a welcome advance in the art.

For example, traditional $CO_2$ sensors consume quite a bit of power to accurately read levels of $CO_2$ in the local environment. The NDIR (non-dispersive infra-red) process that sensors presently use includes multiple factors that affect the power consumption. The technology of measuring the absorption of light due to the presence of $CO_2$ requires the generation of a specific light frequency at a known power level, which is energy intensive. In some instances, the received light intensity fluctuates, thereby making the individual measurements "noisy." Sensors typically take multiple readings in succession and average or filter them together to reduce the effect of noise, and to present a more stable and accurate value as the output of the sensor. However, each sensor sample uses some discrete amount of total battery energy.

SUMMARY

In accordance with at least one aspect, the present disclosure is directed to a method for reducing power consumption of a sensor. The method includes determining if a predetermined condition has been met to change at least one of a sensing rate or a sensor resolution, and changing at least one of the sensing rate or sensor resolution if it is determined that the predetermined condition has been met.

In another aspect, the method may include sensing a monitored gas in a local atmosphere.

In another aspect, sensing the amount of the monitored gas may include sensing at least one of ethylene, CO, methane, $O_2$, $H_2S$, $CO_2$, or other volatile organic compound gases.

In another aspect, determining if the predetermined condition has been met may include determining an amount or proportion of the monitored gas in the local atmosphere.

In another aspect, determining if the predetermined condition has been met may include determining a rate of change of the amount of the monitored gas over a time.

In another aspect, determining if the predetermined condition has been met may include comparing the rate of change of the amount of the monitored gas to a threshold rate of change to determine whether to change the sensing rate or sensor resolution.

In another aspect, determining if the predetermined condition has been met may include determining an occupancy state of a building.

In another aspect, determining the occupancy state may include referencing a predetermined schedule and comparing a local clock to the predetermined schedule to determine the occupancy state of the building.

In another aspect, changing the sensing rate or the sensor resolution may include reducing the sensing rate or the sensor resolution to a minimum safe sensing rate or minimum safe sensor resolution.

In another aspect, reducing the sensing rate may include reducing the sensing rate from about 1 sensing per minute to about 1 sensing per hour.

In another aspect, reducing the sensor resolution may include reducing an amount of samples per sensor reading.

In accordance with another aspect of this disclosure, a sensor for an HVAC system includes a processor and a memory, and an energy management module stored in the memory and configured to be executed by the processor. The energy management module is configured for determining if a predetermined condition has been met to change at least one of a sensing rate or a sensor resolution, and changing at least one of the sensing rate or sensor resolution if it is determined that the predetermined condition has been met.

In another aspect, determining if the predetermined condition has been met may include determining an amount or proportion of a monitored gas in a local atmosphere.

In another aspect, determining if the predetermined condition has been met may include determining a rate of change of the amount of the monitored gas over a time.

In another aspect, determining if the predetermined condition has been met may include comparing the rate of change of the amount of the monitored gas to a threshold rate of change to determine whether to change the sensing rate or sensor resolution.

In another aspect, determining if the predetermined condition has been met may include determining an occupancy state of a building.

In another aspect, determining the occupancy state may include referencing a predetermined schedule and comparing a local clock to the predetermined schedule to determine the occupancy state of the building.

In another aspect, changing the sensing rate or the sensor resolution may include reducing the sensing rate or the sensor resolution to a minimum safe sensing rate or minimum safe sensor resolution.

In another aspect, reducing the sensing rate may include reducing the sensing rate from about 1 sensing per minute to about 1 sensing per hour.

In another aspect, reducing the sensor resolution may include reducing an amount of samples per sensor reading.

In accordance with another aspect of this disclosure, a system for reducing power consumption of sensors includes at least one computer server configured to be in communication with at least one sensor, and a power management module stored on the server. The energy management module is configured for determining if a predetermined condition has been met to change at least one of a sensing rate or a sensor resolution of the at least one sensor, and changing at least one of the sensing rate or sensor resolution if it is determined that the predetermined condition has been met.

In another aspect, determining if the predetermined condition is met may include receiving condition data from the sensor.

In another aspect, changing at least one of the sensing rate or sensor resolution may include outputting a command to the sensor to change at least one of the sensing rate or the sensor resolution.

BRIEF DESCRIPTION OF THE DRAWINGS

Various embodiments of the disclosed system and method are described herein with reference to the drawings wherein.

Figure 1:
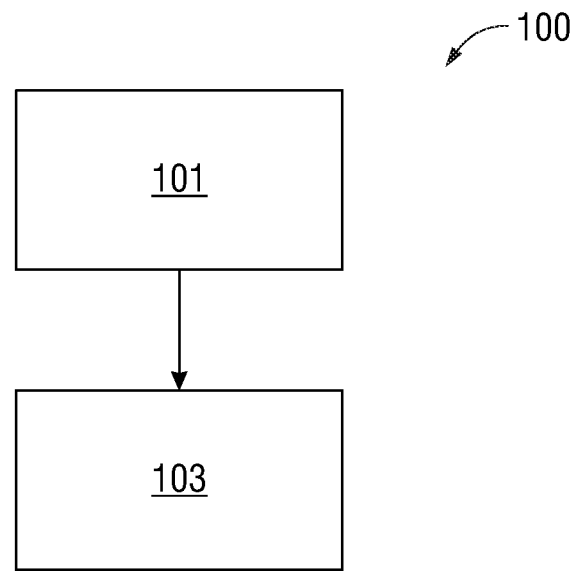
FIG. 1 is flow chart of an embodiment of a method in accordance with the present disclosure.

The various aspects of the present disclosure mentioned above are described in further detail with reference to the aforementioned figures and the following detailed description of exemplary embodiments.

DETAILED DESCRIPTION

Particular illustrative embodiments of the present disclosure are described hereinbelow with reference to the accompanying drawings; however, the disclosed embodiments are merely examples of the disclosure, which may be embodied in various forms. Well-known functions or constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In this description, as well as in the drawings, like-referenced numbers represent elements which may perform the same, similar, or equivalent functions. The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

The present disclosure is described herein in terms of functional block components and various processing steps. It should be appreciated that such functional blocks and/or processing steps may be realized by any number of hardware and/or software components configured to perform the specified functions. For example, the present disclosure may employ various integrated circuit components, e.g., memory elements, processing elements, logic elements, look-up tables, and the like, which may carry out a variety of functions under the control of one or more microprocessors or other control devices.

Similarly, the software elements of the present disclosure may be implemented with any programming or scripting language such as C, C++, C#, Java, COBOL, assembler, PERL, Python, PHP, or the like, with the various algorithms being implemented with any combination of data structures, objects, processes, routines or other programming elements. The object code created may be executed by any device, on a variety of operating systems, including without limitation RTOS, Apple OSX®, Apple iOS®, Google Android®, HP WebOS®, Linux, UNIX®, Microsoft Windows®, and/or Microsoft Windows Mobile®.

It should be appreciated that the particular implementations described herein are illustrative of the disclosure and its best mode and are not intended to otherwise limit the scope of the present disclosure in any way. Examples are presented herein which may include data items which are intended as examples and are not to be construed as limiting. Indeed, for the sake of brevity, conventional data networking, application development and other functional aspects of the systems (and components of the individual operating components of the systems) may not be described in detail herein. It should be noted that many alternative or additional functional relationships or physical or virtual connections may be present in a practical electronic system or apparatus. In the discussion contained herein, the terms user interface element and/or button are understood to be non-limiting, and include other user interface elements such as, without limitation, pushbutton, a proximity sensor, a hyperlink, clickable image, and the like.

As will be appreciated by one of ordinary skill in the art, aspects of the present disclosure may be embodied as a method, a data processing system, a device for data processing, and/or a computer program product. Certain aspects of the present disclosure may take the form of a computer program product on a computer-readable storage medium having computer-readable program code means embodied in the storage medium. Any suitable computer-readable storage medium may be utilized, including hard disks, CD-ROM, DVD-ROM, optical storage devices, magnetic storage devices, semiconductor storage devices (e.g., EEPROM, mask ROM, flash memory, USB thumb drives) and/or the like.

Computer program instructions embodying certain aspects of the present disclosure may also be stored in a computer-readable memory that may direct a computer or other programmable data processing apparatus to function in a particular manner, such that the instructions stored in the computer-readable memory produce an article of manufacture, including instruction means, that implement the function specified in the description or flowchart block(s). The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the present disclosure.

One skilled in the art will also appreciate that, for security and/or any other suitable reason, any components, data structures, and communications links may include any of various suitable security features, such as firewalls, access codes, encryption, de-encryption, compression, decompression, and/or the like. In some instances, the steps recited herein may be executed in any order and are not limited to the order presented.

Certain embodiments are disclosed herein which operate in accordance with the ZigBee® wireless mesh networking standards, however, it should be understood that embodiments of the present disclosure are applicable to any wired or wireless network architecture, including without limitation Z-Wave®, in which the features and advantages discussed herein may be advantageously employed.

Referring to FIG. 1, in accordance with the present disclosure, a method 100 for reducing power consumption of a sensor (e.g., a $CO_2$ sensor or any other suitable sensor) includes determining (e.g., in block 101) if a predetermined condition has been met to change at least one of a sensing rate or a sensor resolution, and changing (e.g., in block 103) at least one of the sensing rate or sensor resolution if it is determined that the predetermined condition has been met.

The method 100 may include sensing a monitored gas in a local atmosphere (e.g., where the sensor is located). In certain embodiments, sensing the amount of the monitored gas may include sensing at least one of ethylene, CO, methane, $O_2$, $H_2S$, $CO_2$, or other volatile organic compound gases.

Determining 101 if the predetermined condition has been met may include determining an amount or proportion of the monitored gas in the local atmosphere. Determining 101 if the predetermined condition has been met may include determining a rate of change of the amount of the monitored gas over a time. For example, determining 101 if the predetermined condition has been met may include comparing the rate of change of the amount of the monitored gas to a threshold rate of change to determine whether to change the sensing rate or sensor resolution.

In such a case, if a rate of change of the monitored gas is below the threshold rate of change, it can be determined that the predetermined condition has been met to reduce sensor resolution and/or sensing rate. This may allow less use of energy resources while ensuring that no unsafe conditions are created.

In certain embodiments, determining 101 if the predetermined condition has been met may include determining an occupancy state of a building. For example, determining the occupancy state may include referencing a predetermined schedule and comparing a local clock (e.g., on the sensor) to the predetermined schedule to determine the occupancy state of the building. In certain embodiments, determining 101 if the predetermined condition has been met may include determining if an HVAC system is in an off state such that a reading would go wasted (e.g., which can be a function of occupancy state).

In certain embodiments, e.g., after block 101 as described above, changing 103 the sensing rate or the sensor resolution may include reducing the sensing rate or the sensor resolution to a minimum safe sensing rate or minimum safe sensor resolution. In this case, a predetermined minimum safe time-lapse or error value can be calculated to estimate that the sensed condition (e.g., $CO_2$ levels) cannot rise above a threshold safety level in the time between sensing and/or accounting for error due to resolution. It is contemplated that such minimum safe rates or resolutions can be calculated to any suitable degree of certainty based on any suitable criteria (e.g., past $CO_2$ levels data for the location of the sensor such as maxima, minima, averages, date/time correlations, environmental correlations).

In certain embodiments, reducing the sensing rate may include reducing the sensing rate from about 1 sensing per minute to about 1 sensing per hour. Any other suitable sensing rate reduction is contemplated herein. It is also contemplated that changing 101 can include increasing the sensing rate (e.g., from about 1 hour to about 1 min) if the predetermined condition to reduce the sensing rate is lost at any suitable point after reducing the sensing rate.

In certain embodiments, reducing the sensor resolution may include reducing an amount of samples per sensor reading. For example, certain sensors may take a plurality of samples (e.g., simultaneously or successively) at a given reading to account for noise reduction of the reading. Reducing the amount of samples at each reading can reduce the accuracy/resolution of each reading due to less noise/error cancellation. Since each sample requires a discrete amount of energy for a powered sensor, a reduction in samples can reduce energy consumption. As is appreciated by those ordinarily skilled in the art, the sample amount can be reduced to a minimum safe resolution as described above.

In certain embodiments, the method 100 can include using a fixed schedule of sensing rate and/or sensor resolution to modify the performance of the sensor 200. In other embodiments, it is contemplated that the new sensing rate and/or sensor resolution can be calculated (e.g., by the sensor 200) in real time or in any suitable interval.

Figure 2:
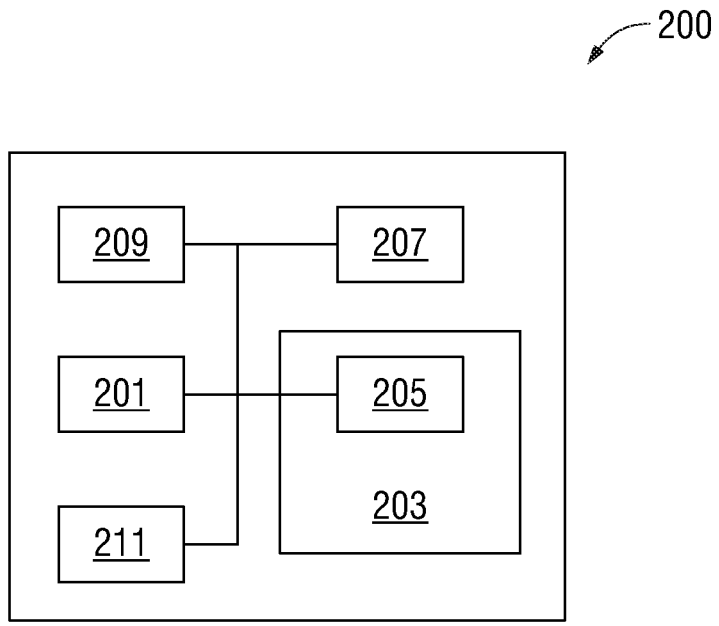
FIG. 2 is a schematic diagram of an embodiment of a sensor in accordance with the present disclosure.

Referring to FIG. 2, in accordance with another aspect of this disclosure, a sensor 200 for an HVAC system (e.g., a $CO_2$ sensor) may include a processor 201, a memory 203, and an energy management module 205 stored in the memory 203 that is configured to be executed by the processor 205. The energy management module 205 may include any suitable logic hardware and/or software to execute an energy management routine (e.g., method 100). The energy management module 205 can be configured to perform any suitable portion or all of method 100 as described above. The sensor 200 may be battery powered or powered via any other suitable means.

For example, energy management module 205 may be configured for determining if a predetermined condition has been met to change at least one of a sensing rate or a sensor resolution. The energy management module 205 may also be configured to change at least one of the sensing rate or sensor resolution if it is determined that the predetermined condition has been met. Any and all other suitable portions of method 100 may or may not be performed by energy management module 205.

Figure 3:
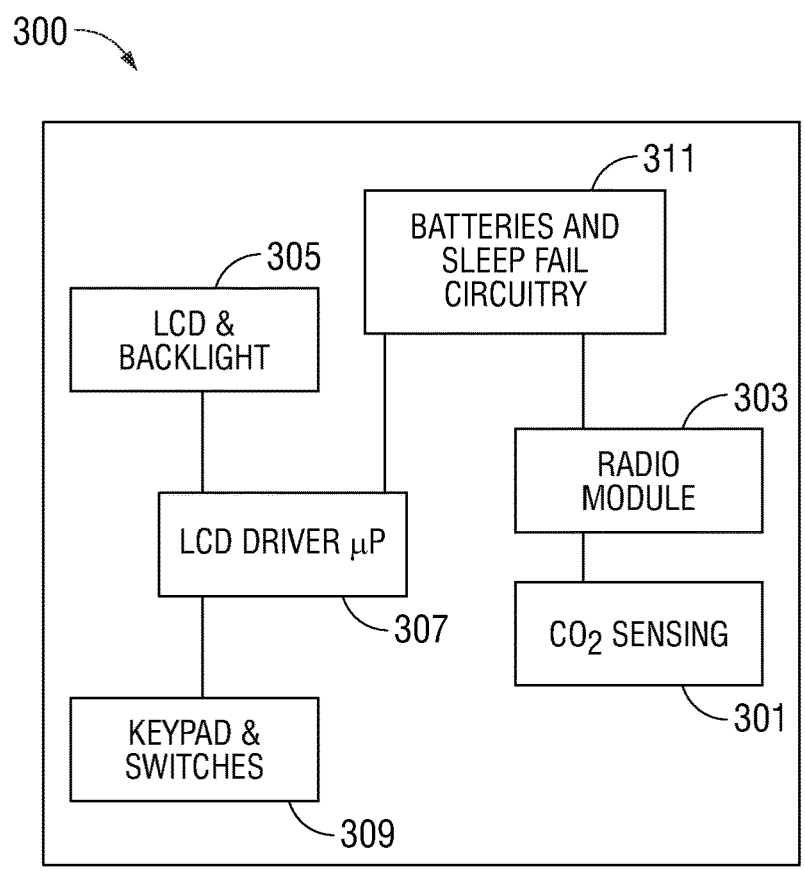
FIG. 3 is a schematic diagram of an embodiment of a $CO_2$ sensor in accordance with the present disclosure.

Referring to FIG. 3, an embodiment of a sensor device 300 for an HVAC system is shown. The sensor device 300 includes a $CO_2$ sensor 301 and a radio module 303 that is connected to the $CO_2$ sensor 301. The $CO_2$ sensor 301 may include any suitable portions or all of sensor 200 as described above (e.g., energy management module 205), and/or any other suitable features. For example, the sensor device 300 may include an LCD display 305 (e.g., including a backlight) operatively connected to an LCD driver 307 to display images (e.g., numbers, letters) on the LCD display 305. The sensor device 300 can also include a keypad and/or one or more switches 309 which allow a user to input commands into the sensor device 300. The sensor device 300 can also include one or more batteries 311 as well as other suitable circuitry (e.g., sleep fail circuitry to prevent a sleep mode failure).

In certain embodiments, an input indication that the sensor 301 is in safe mode may be programmed and/or manually switched by a user before or after placing the sensor 301 into service. For example, if a user knows that the location or intended use of a particular sensor 301 requires full time maximum sensing for liability or safety reasons, then the user may operate a suitable control (e.g., the keypad and/or switches 309, a touch screen display, a digital command from a remote device) to instruct the energy management module 205 to shut off and/or avoid changing the sensing rate and/or sensor resolution.

Figure 4:
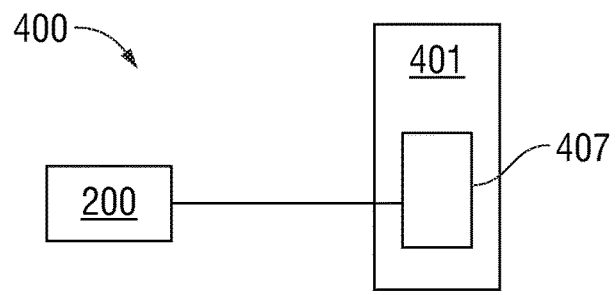
FIG. 4 is a schematic diagram of an embodiment of a system in accordance with the present disclosure.

Referring to FIGS. 2 and 4, the sensor (e.g., sensor 200 as shown) can be part of a system 400 for managing energy usage of one or more sensors 200 (e.g., for reducing power consumption of sensors 200). For example, the sensor 200 can be configured to be connected (wired or wireless) to remote server 401. The energy management module 200 may alternatively and/or additionally be configured to receive energy management data (e.g., through transmitter/receiver (TX/RX) 209) from a power management module 407 of a remote server 401. In such a case, the energy management module 205 may or may not include one or more portions of method 100, and power management module 407 may be configured to operate at least one suitable portion of method 100. For example, the power management module 407 can perform the functions of the energy management module as described above to provide a sensor 200 with data/instruction to reduce sensing rate and or sensor resolution.

In this regard, primary sensor 207 can take readings and provide data to the memory 203 and/or energy management module 205. The sensor 200 may also include a state sensor 211 for sensing one or more suitable conditions of the sensor 200 or environment around the sensor 200 (e.g., temperature, pressure, age of the sensor) in addition to the primary sensor 207 (e.g., $CO_2$ sensing element). Such data can be received by the energy management module 205.

The energy management module 205 can then transmit one or more data points (e.g., a plurality of data points of a period of time) to the power management module 407 of the remote server 401 via the TX/RX 209. The energy management module 205 may additionally or alternatively send a request for energy management to the server 401 in order to notify the power management module 407 that the sensor 200 requires power management instruction from the server 401. The power management module 407 may include a subroutine to provide similar instructions to any other sensors 200 in a related group (e.g., all similar sensors in a given location), for example.

The power management module 407 may use the data received from the energy management module 205 of the sensor 200 and use it to determine if one or more predetermined conditions have been met (e.g., sensor variance below a threshold, building occupancy status) as described above with respect to method 100. The power management module 407 may then output a command to the sensor 200 to cause the sensor 200 to change (e.g., reduce) the sensing rate and/or the sensor resolution if it is determined that the predetermined condition has been met.

For example, occupancy information can be sent to the sensor 200 either as a state variable (occupied or unoccupied) or as a time remaining until the mode changes to occupied. Similarly the desired level of resolution can be communicated to the sensor 200 to allow the sensor 200 to provide the proper level of significant digits in the reported value.

While embodiments of this disclosure are directed to sensors (e.g., battery powered $CO_2$ sensors) it is contemplated that the methods and systems described herein may be implemented on any suitable powered electronic device for energy usage management, whether battery powered or not.

Utilizing the hereinabove described systems, devices, and methods, limited power in the batteries can be conserved allowing for the operable life of sensors to increase substantially (e.g, by double). For example, readings can be taken only when needed (e.g., only when the HVAC control system is on) and/or the resolution of each reading can be reduced to avoid expending energy when it is unnecessary (e.g., when a building is in a steady state and/or unoccupied).

Aspects

It is noted that any of aspects described below can be combined with each other in any suitable combination as is appreciated by those having ordinary skill in the art.

Aspect 1. A method for reducing power consumption of a sensor. The method includes determining if a predetermined condition has been met to change at least one of a sensing rate or a sensor resolution, and changing at least one of the sensing rate or sensor resolution if it is determined that the predetermined condition has been met.

Aspect 2. The method may include sensing a monitored gas in a local atmosphere.

Aspect 3. Sensing the amount of the monitored gas may include sensing at least one of ethylene, CO, methane, $O_2$, $H_2S$, $CO_2$, or other volatile organic compound gases.

Aspect 4. Determining if the predetermined condition has been met may include determining an amount or proportion of the monitored gas in the local atmosphere.

Aspect 5. Determining if the predetermined condition has been met may include determining a rate of change of the amount of the monitored gas over a time.

Aspect 6. Determining if the predetermined condition has been met may include comparing the rate of change of the amount of the monitored gas to a threshold rate of change to determine whether to change the sensing rate or sensor resolution.

Aspect 7. Determining if the predetermined condition has been met may include determining an occupancy state of a building.

Aspect 8. Determining the occupancy state may include referencing a predetermined schedule and comparing a local clock to the predetermined schedule to determine the occupancy state of the building.

Aspect 9. Changing the sensing rate or the sensor resolution may include reducing the sensing rate or the sensor resolution to a minimum safe sensing rate or minimum safe sensor resolution.

Aspect 10. Reducing the sensing rate may include reducing the sensing rate from about 1 sensing per minute to about 1 sensing per hour.

Aspect 11. Reducing the sensor resolution may include reducing an amount of samples per sensor reading.

Aspect 12. A sensor for an HVAC system includes a processor and a memory, and an energy management module stored in the memory and configured to be executed by the processor. The energy management module is configured for determining if a predetermined condition has been met to change at least one of a sensing rate or a sensor resolution, and changing at least one of the sensing rate or sensor resolution if it is determined that the predetermined condition has been met.

Aspect 13. Determining if the predetermined condition has been met may include determining an amount or proportion of a monitored gas in a local atmosphere.

Aspect 14. Determining if the predetermined condition has been met may include determining a rate of change of the amount of the monitored gas over a time.

Aspect 15. Determining if the predetermined condition has been met may include comparing the rate of change of the amount of the monitored gas to a threshold rate of change to determine whether to change the sensing rate or sensor resolution.

Aspect 16. Determining if the predetermined condition has been met may include determining an occupancy state of a building.

Aspect 17. Determining the occupancy state may include referencing a predetermined schedule and comparing a local clock to the predetermined schedule to determine the occupancy state of the building.

Aspect 18. Changing the sensing rate or the sensor resolution may include reducing the sensing rate or the sensor resolution to a minimum safe sensing rate or minimum safe sensor resolution.

Aspect 19. Reducing the sensing rate may include reducing the sensing rate from about 1 sensing per minute to about 1 sensing per hour.

Aspect 20. Reducing the sensor resolution may include reducing an amount of samples per sensor reading.

Aspect 21. A system for reducing power consumption of sensors includes at least one computer server configured to be in communication with at least one sensor, and a power management module stored on the server. The energy management module is configured for determining if a predetermined condition has been met to change at least one of a sensing rate or a sensor resolution of the at least one sensor, and changing at least one of the sensing rate or sensor resolution if it is determined that the predetermined condition has been met.

Aspect 22. Determining if the predetermined condition is met may include receiving condition data from the sensor.

Aspect 23. Changing at least one of the sensing rate or sensor resolution may include outputting a command to the sensor to change at least one of the sensing rate or the sensor resolution.

Particular embodiments of the present disclosure have been described herein, however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in any appropriately detailed structure.

What is claimed is:

1. A method for reducing power consumption of a sensor, comprising:
sensing a monitored gas in a local atmosphere by taking sensor readings at a sensing rate, wherein each sensor reading comprises an amount of individual samples;
determining if a predetermined condition has been met to change at least one of a sensing rate or the amount of individual samples comprising each sensor reading; and
changing the amount of individual samples comprising each sensor reading if it is determined that the predetermined condition has been met.

2. The method of claim 1, wherein sensing the amount of the monitored gas includes sensing at least one of ethylene, CO, methane, $O_2$, $H_2S$, and/or $CO_2$.

3. The method of claim 1, wherein determining if the predetermined condition has been met includes determining an amount and/or a proportion of the monitored gas in the local atmosphere.

4. The method of claim 1, wherein determining if the predetermined condition has been met includes determining a rate of change of the amount and/or a proportion of the monitored gas over a time.

5. The method of claim 4, wherein determining if the predetermined condition has been met includes comparing the rate of change of the amount and/or a proportion of the monitored gas to a threshold rate of change to determine whether to change the sensing rate or sensor resolution.

6. The method of claim 1, wherein determining if the predetermined condition has been met includes determining an occupancy state of a building.

7. The method of claim 6, wherein determining the occupancy state includes referencing a predetermined schedule and comparing a local clock to the predetermined schedule to determine the occupancy state of the building.

8. The method of claim 1, wherein changing the amount of individual samples comprising each sensor reading includes reducing the amount of individual samples comprising each sensor reading to a minimum safe sensor resolution.

9. The method of claim 8, wherein reducing the sensing rate includes reducing the sensing rate from about 1 sensing per minute to about 1 sensing per hour.

10. The method of claim 1, wherein determining if the predetermined condition has been met includes include determining if an HVAC system is in an off state.

11. A sensor for an HVAC system, comprising:
a processor operatively coupled to a memory; and
an energy management module stored in the memory and configured to be executed by the processor, the energy management module configured for:
sensing a monitored gas in a local atmosphere by taking sensor readings at a sensing rate, wherein each sensor reading comprises an amount of individual samples;
determining if a predetermined condition has been met to change at least one of a sensing rate or the amount of individual samples comprising each sensor reading; and
changing the amount of individual samples comprising each sensor reading if it is determined that the predetermined condition has been met.

12. The sensor of claim 11, wherein determining if the predetermined condition has been met includes determining a rate of change of the amount and/or a proportion of the monitored gas over a time.

13. The sensor of claim 12, wherein determining if the predetermined condition has been met includes comparing the rate of change of the amount and/or a proportion of the monitored gas to a threshold rate of change to determine whether to change the sensing rate and/or sensor resolution.

14. The sensor of claim 11, wherein determining if the predetermined condition has been met includes determining an occupancy state of a building.

15. The sensor of claim 14, wherein determining the occupancy state includes referencing a predetermined schedule and comparing a local clock to the predetermined schedule to determine the occupancy state of the building.

16. The sensor of claim 11, wherein changing the amount of individual samples comprising each sensor reading includes reducing the amount of individual samples comprising each sensor reading to a minimum safe sensor resolution.

17. The sensor of claim 16, wherein reducing the sensing rate includes reducing the sensing rate from about 1 sensing per minute to about 1 sensing per hour.

18. The sensor of claim 11, wherein determining if the predetermined condition has been met includes include determining if an HVAC system is in an off state.

19. A system for reducing power consumption of sensors, comprising:
- at least one computer server configured to be in communication with at least one sensor; and
- a power management module stored on the server, the power management module configured for:
- determining if a predetermined condition has been met to change at least one of a sensing rate and/or a the amount of individual samples comprising each sensor reading of the at least one sensor; and
- changing the amount of individual samples comprising each sensor reading if it is determined that the predetermined condition has been met.

20. The system of claim 19, wherein determining if the predetermined condition is met includes receiving condition data from the sensor.

21. The system of claim 19, wherein changing the amount of individual samples comprising each sensor reading includes outputting a command to the sensor to change the amount of individual samples comprising each sensor reading.

22. The system of claim 19, wherein determining if the predetermined condition is met includes determining if an HVAC system is in an off state.

* * * * *